United States Patent [19]

Bowditch

[11] 4,417,033

[45] Nov. 22, 1983

[54] DIGLYCIDYL ETHER OF DIMETHANOL CYCLOHEXANE AND REACTION PRODUCTS THEREOF

[75] Inventor: W. Raymond Bowditch, West Chester, Pa.

[73] Assignee: Wilmington Chemical Corporation, Wilmington, Del.

[21] Appl. No.: 383,480

[22] Filed: Jun. 1, 1982

[51] Int. Cl.$^3$ ............................................. C08G 59/24
[52] U.S. Cl. .................................... 525/481; 525/524; 528/87
[58] Field of Search .................... 525/481, 524; 528/87

[56] References Cited

U.S. PATENT DOCUMENTS

| | | | |
|---|---|---|---|
| 3,297,724 | 1/1967 | McConnell et al. | 260/348 |
| 3,379,684 | 4/1968 | Wiesner et al. | 528/87 X |
| 3,395,128 | 7/1968 | Hale et al. | 528/367 |
| 3,948,855 | 4/1976 | Perry | 528/87 X |

Primary Examiner—Earl A. Nielsen
Attorney, Agent, or Firm—Webb, Burden, Robinson & Webb

[57] ABSTRACT

A difunctional epoxide along with reaction products thereof is disclosed. The epoxide is represented by the structural formula:

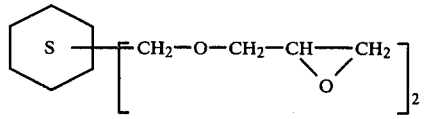

Improved epoxy resins prepared by the advancement reaction of the above epoxide with polyhydric phenols are also disclosed.

3 Claims, No Drawings

DIGLYCIDYL ETHER OF DIMETHANOL CYCLOHEXANE AND REACTION PRODUCTS THEREOF

BACKGROUND OF THE INVENTION

1. Field of the Invention

This invention relates to epoxy resins, and more particularly, diepoxides and reaction products thereof.

2. Description of the Prior Art

Epoxy resins and polyfunctional epoxide compounds have found extensive utility in the field of coating, molding and the like. These polyfunctional epoxides and epoxy resins include the reaction products of dihydric phenols and halohydrins with subsequent dehydrohalogenation to produce epoxides tailored for particular purposes. Undoubtedly, the two types of epoxides which have been found to have the broadest range of properties useful in a plurality of applications are those based upon bisphenol A and epichlorohydrin and those based upon the condensation products of formaldehyde and phenol with subsequent epoxidation with epichlorohydrin. Those epoxy resins which are based upon the epoxidized phenol-formaldehyde condensation products are commonly referred to as novolak resins, and those based upon bisphenol A and epichlorohydrin are known as the Epon ® resins which are manufactured by Shell Chemical Company.

These novolak and Epon resins vary in molecular weight and epoxide equivalent, with these factors being determinative of particular applications for their use.

In most cases, these specific epoxides, even with additional modifications, are limited in one way or another in their applicability to only a narrow range of uses. One determinative factor in selecting an epoxide for a particular use is viscosity. The viscosity of a particular epoxide to a large degree limits the uses to which the epoxide can be made. In the manufacture of coatings, as an example, it is undesirable to use coating formulations which have ranges of viscosity which are either so low that the formulation flows off the surface being coated or so high that it is difficult to apply without the addition of heat and without encountering rheological problems.

Similarly, in applications such as casting, molding or bonding parts and the like, it is desirable to have a relatively low viscosity epoxide which quickly and completely fills mold and interstices. Further, low viscosity formulations are capable of accepting larger amounts of fillers, pigments and the like over higher viscosity epoxies.

Still further, with present environmental constraints upon the use of volatile solvents, it has been a goal in the coating industry to eliminate the use of such solvents and utilize 100 percent solids systems. Such systems are practical when the viscosity of the 100 percent solids systems, i.e. in this instance the epoxy resin, is relatively low.

When epoxy resins are used in molding, casting and the like where thick masses of cured epoxy resin or polyfunctional epoxide are produced, it is necessary to have a 100 percent nonvolatile content in the resin or polyepoxide since it is difficult for solvents and the like to be released from the mass during curing, which often results in voids within the mass which are undesirable. Likewise, when epoxies are used for bonding parts as thermoset adhesives, it is desirable to have a 100 percent reactive system without the addition of solvents.

Although many polyepoxides and epoxy resins have been synthesized from various starting materials resulting in aliphatic, alicyclic and phenolic polyepoxides and epoxy resins, by far the most widely used epoxides on a commercial basis have been the Epon and novolak type resins due to their cost and final physical properties for particular applications.

The primary disadvantages of these Epon and novolak type resins are that they have high viscosities relative to molecular weight and require diluents or environmental modifications during application, such as heat and the like, to be used for particular applications.

In order to alleviate this disadvantage, workers in the art have provided reactive diluents such as low molecular weight mono- and polyepoxides which act as a viscosity reducer for the phenolic-based epoxy resins and which react within the system to form 100 percent solids coating and molding resins.

In many instances, these low viscosity diluents are formed by the peroxidation of ethylenically unsaturated materials. Further, other low viscosity epoxides have been produced by the epoxidation of alcohols, diols and polyols with epichlorohydrin.

Exemplary of various epoxy resins and polyepoxides which have been used as reactive diluents and also as reactive compositions alone are those disclosed in U.S. Pat. Nos. 2,925,403; 3,444,111; 3,470,110; 3,477,990; 3,547,881; 3,838,175; 4,119,593; 3,138,618 and 3,379,653. Most of these epoxides which are of low viscosity and having been used as diluents are the alicyclic epoxides which are formed by the peroxidation of cycloalkenes.

While it is recognized that the epoxy group can be catalyzed and is reactive with amines, carboxylic acids, Lewis acids and the like, different epoxides function differently in these environments. For example, it is recognized that the phenolic-based epoxides are more highly reactive with amines and quaternary ammonium salts than are the alicyclic epoxides, whereas the alicyclic epoxides are more reactive with Lewis acids and carboxylic acids than the phenolic epoxides.

Thus, when a low molecular weight functional epoxide is used as a reactive diluent with a phenolic epoxide, there may be difficulty in obtaining a complete reaction among the epoxides in the composition because of the difference in catalysis and crosslinking rate.

In accordance with the present invention, a low molecular weight diepoxide is provided which is useful as the sole epoxy constituent in forming coatings, moldings and the like and is further useful as a reactive diluent for phenolic epoxides. In addition, the difunctional epoxide in accordance with the invention, when copolymerized with phenolic compounds upon which epoxy resins are normally based, is effective in reducing the viscosity of the final epoxy resins while not deteriorating and sometimes enhancing the final properties of the product to be formed.

BRIEF DESCRIPTION OF THE INVENTION

A difunctional epoxide is provided which is represented by the structural formula:

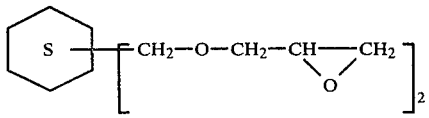

In addition, an epoxy resin is provided which is comprised of the reaction product of the above diepoxide and a polyfunctional phenolic hydroxy compound represented by the structural formula:

wherein R is an aromatic residue and m is at least 2. The resultant reaction product is at least difunctional in epoxide groups.

DETAILED DESCRIPTION OF THE INVENTION

The diepoxide which is represented by the structural formula:

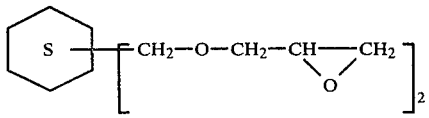

is synthesized by reacting cyclohexane dimethanol with an epihalohydrin in the presence of a suitable catalyst. Subsequent to the reaction of the epihalohydrin with the cyclohexane dimethanol to form the reacted chlorohydrin, the chlorohydrin is dehydrohalogenated to form the diepoxide. Typically, a stoichiometric excess of 8 to 10 percent of the epihalohydrin is used in relation to the equivalents of hydroxyl on the cyclohexane dimethanol.

The epihalohydrins useful in the practice of the invention in forming the diepoxide are epichlorohydrin and epibromohydrin. Epichlorohydrin is preferred. The reaction between the epihalohydrin and the cyclohexane dimethanol is done in the presence of a base such as sodium hydroxide, potassium hydroxide or the like, at a concentration of 1.05 to 1.06 or greater moles of hydroxide per equivalent of hydroxyl. The processing steps in forming epoxies from diols and epihalohydrins are well known to those skilled in the art.

In another aspect of the invention, the cyclohexane dimethanol diglycidyl ether which is in accordance with the invention is reacted with a polyfunctional phenolic hydroxyl compound. These polyfunctional hydroxyl compounds can be represented by the structural formula:

wherein R is an aromatic residue and m is at least 2. The stoichiometry is adjusted such that the reaction product is at least difunctional and thus a stoichiometry of 2 moles of the cyclohexane dimethanol diglycidyl ether to 1 mole of difunctional phenolic compound is required. When higher molecular weight versions of the reaction product are desired, the OH equivalent to epoxy equivalent approaches equality, but in all instances a sufficient excess of the diepoxide must be provided in order to have residual reactive epoxide compounds in the final resin in accordance with the invention. Thus, the range of equivalents between hydroxyl to epoxide in accordance with the invention is in the range of greater than 1 equivalent of diepoxide to 1 equivalent of hydroxyl and 2 equivalents of diepoxide to 1 of hydroxyl. Most preferably, the reactive hydroxyl is an aromatic hydroxyl. Typical R—[OH]$_m$ compounds can be represented by the structural formula:

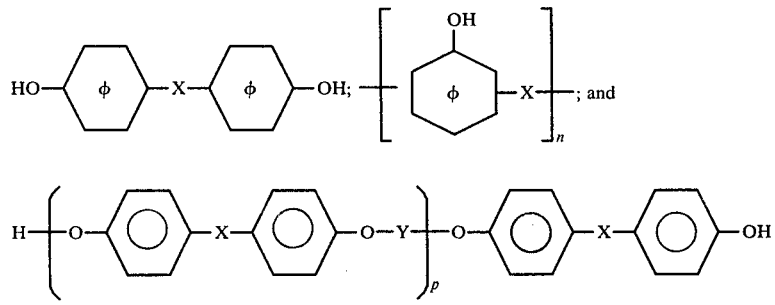

wherein X is alkylene having 1 to 3 carbon atoms, n and p are greater than 1, and Y is selected from the group consisting of:

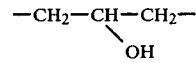

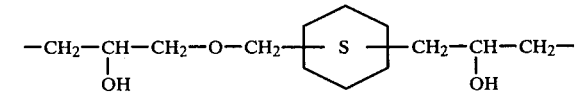

Among the polyfunctional phenolic hydroxy compounds recited above, the following are the most preferred: bisphenol A, resorcinol and bisphenol F, and novolak resins having a hydroxyl functionality of 3 to 5 and having a molecular weight range of 320 to 600, and polymeric materials which are provided by the reaction of the diglycidyl ether of cyclohexane dimethanol and the difunctional phenols such as bisphenol A and bisphenol F, wherein a copolymer is prepared having alternating bisphenolic and beta-hydroxypropyl ether of cyclohexane dimethanol moieties throughout the chain. In the latter instance, lower viscosities are achieved in relation to comparable molecular weight phenolic epoxies based solely on the bisphenol and epichlorohydrin.

In reacting the diglycidyl ether of cyclohexane dimethanol and the phenolic compound, suitable quantities of the diglycidyl ether and polyfunctional phenolic hydroxy compound are charged to a suitable vessel and a catalyst is added. The reaction is allowed to proceed so that an epoxy-terminated material is formed. Subsequent to the initial reaction, additional diglycidyl ether may be charged to reduce the viscosity of the final product.

The reaction is conducted between 155° and 190° C. for 4 to 7 hours to insure complete reaction between the phenolic compound and the epoxide.

The catalysts useful in the practice of the invention are the tertiary amines and quaternary ammonium salts. Typical catalysts are 2-methylimidazole, tetramethylammonium chloride, tetramethylammonium bromide, alkali hydroxides and the like.

After it is determined that the desired epoxide has been formed, it is cooled to room temperature or dissolved in a solvent. These epoxides may be cured by amine or acid catalysts recognized by those skilled in the art for curing epoxy resins.

It has been found that the epoxy resins prepared in accordance with the invention are useful as 100 percent solids coatings, moldings and the like. Additionally, epoxides, which are the copolymeric epoxides, have substantially reduced viscosities over comparable epoxides synthesized from solely phenolic hydroxy compounds and epihalohydrins.

The following examples will more fully illustrate the invention:

EXAMPLE I

In a three-liter three-neck glass reaction flask, equipped with a thermometer, stirrer, condenser and dropping funnel were placed cyclohexane dimethanol, toluene and the catalyst. Epichlorohydrin was then added gradually through the dropping funnel to the mixture at such a rate that the temperature varied from 70° to 90° C., with external cooling being applied to the flask. Sodium hydroxide was then added which dehydrohalogenated the chlorohydrin intermediate and neutralized the formed hydrochloric acid. After removal of salt, the mixture was dried and filtered to yield pure diglycidyl ether of cyclohexane dimethanol. The weight per epoxide of the reaction product was 158 to 168, with a viscosity of 60 to 70 centipoise.

EXAMPLE II

To an appropriate vessel which has been flushed with inert gas were charged 2500 parts by weight of the diepoxide of Example I, 812.5 parts of bisphenol A, and 0.165 parts by weight of 2-methylimidazole. The charge was agitated and heated to 150° to 155° C. under inert gas with agitation. The reaction was exothermic and reached 190° to 195° C. At this point, 812.5 parts by weight of bisphenol A were charged to the reaction mixture. The exotherm subsided and the mixture was held for 6 hours between 150° to 155° C. After 6 hours the reaction was complete and the product was analyzed. The weight per epoxide of the reaction product was 2891 with a Gardner-Holt viscosity of U to V at 40 percent by weight solids in butyl carbitol.

EXAMPLE III

The procedure of Example II was repeated, except that 2500 parts by weight of the epoxide of Example I, 750 parts of bisphenol A and 0.2 parts by weight of 2-methylimidazole were charged and heated to 150° to 155° C. At exothermic temperature, 750 parts of bisphenol A were charged and the mixture was held for 7 hours between 150° to 155° C. The final product had a weight per epoxide of 2167 and a Gardner-Holt viscosity of T to U at 40 percent solids in butyl carbitol.

EXAMPLE IV

Example II was repeated, except that 2500 parts by weight of epoxide of Example I, 1256 parts by weight of bisphenol A and 1.18 parts by weight of 50 percent caustic soda solution were charged and heated to 150° to 155° C. for 7 hours. The epoxide produced in accordance with this Example IV had a weight per epoxide of 893 and a Gardner-Holt viscosity of G to H at 40 percent solids in butyl carbitol.

EXAMPLE V

Example II was repeated, except that 3000 parts by weight of the epoxide of Example I, 585 parts of bisphenol A and 0.2 parts by weight of 2-methylimidazole were charged and heated to 150° to 155° C. At exothermic temperature, 585 parts of bisphenol A were charged and the mixture was held for 4 hours at 150° to 155° C. The final product had a weight per epoxide of 534 and a Gardner-Holt viscosity of B to C at 40 percent solids in butyl carbitol.

EXAMPLE VI

Example II was repeated, except that 2500 parts by weight of the epoxide of Example I, 714 parts of bisphenol A and 0.2 parts by weight of 2-methylimidazole were charged and heated to 150° to 155° C. At exothermic temperature, 714 parts of bisphenol A were charged and the mixture was held for 5 hours at 150° to 155° C. The epoxide had a weight per epoxide of 1403 and a Gardner-Holt viscosity of K at 40 percent solids in butyl carbitol.

EXAMPLE VII

Example V was repeated, except that the final product was dissolved into 1390 parts by weight of toluene at 80° to 90° C. The resultant solution had a weight per epoxide of 504 and a Gardner-Holt viscosity of V to W at 75 percent solids.

EXAMPLE VIII

Example V was repeated, except that the final product was dissolved into 1390 parts by weight of xylene at 80° to 90° C. The resultant solution had a weight per epoxide of 513 and a Gardner-Holt viscosity of X to Y at 75 percent solids.

EXAMPLE IX

Example II was repeated, except that the final product was dissolved into 2930 parts by weight of cellosolve acetate. The resultant solution had a weight per epoxide of 2914 based on solids and a Gardner-Holt viscosity of $Z_1$ at 57.7 percent solids.

EXAMPLE X

Example II was repeated, except that 2500 parts by weight of the epoxide of Example I, 1800 parts of bisphenol A and 0.2 parts by weight of 2-methylimidazole were charged and heated to 150° to 155° C. After the exotherm, the mixture was held at 155° C. for 7 hours. The epoxide had a weight per epoxide of 4731 and a Gardner-Holt viscosity of U to V at 40 percent solids in butyl carbitol.

Table I illustrates the viscosity of the epoxides prepared in accordance with Examples II through X and the viscosity of comparable epoxides based solely on bisphenol A and epichlorohydrin. The bisphenol A-epichlorohydrin epoxides are described as the Epon resins and the Gardner-Holt viscosities are at 40 percent solids in butyl carbitol.

TABLE I

| Example No. | Weight/Epoxide* | Gardner-Holt Viscosity** | Bisphenol A-Epichlorohydrin Epoxide | Weight/Epoxide | Gardner-Holt Viscosity |
|---|---|---|---|---|---|
| II | 2891 | U–V | 1009 | 2500–4000 | $Z_2$–$Z_5$ |
| III | 2167 | T–U | 1007 | 2000–2500 | Y–$Z_1$ |
| IV | 893 | G–H | 1004 | 850–975 | P–U |
| V | 534 | B–C | 1001 | 450–550 | D–G |
| VI | 1403 | K | — | — | — |
| VII | 504 (Toluene) | V–W | 1001T75 | 450–550 | Z–$Z_5$ |
| VIII | 513 (Xylene) | X–Y | 1001X75 | 450–550 | $Z_3$–$Z_6$ |
| IX | 2914 (Cellosolve Acetate) | $Z_1$ | 1009 | 2500–4000 | — |
| X | 4731 | U–V | 1010 | 4000–6000 | $Z_5$–$Z_7$ |

*Based on Solids
**at 40% NV in butyl carbitol

Table I illustrates that substantially lower viscosity epoxy resins are obtainable in accordance with the invention over comparable epoxy resins based solely on bisphenol A and epichlorohydrin.

Further, when the epoxy resins in accordance with the invention have been used as coatings and molding resins, they have demonstrated equivalent, and in some instances superior, properties over epoxy resins derived solely from bisphenols and epichlorohydrin having comparable epoxy equivalents.

Thus, although the invention has been described with reference to specific processes and specific materials, the invention is only to be limited so far as is set forth in the accompanying claims.

I claim:

1. An epoxy resin comprised of the reaction product of:

(a) a diepoxide represented by the structural formula:

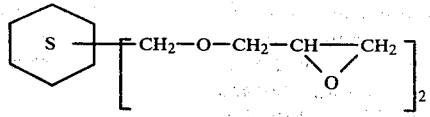

(b) a polyfunctional phenolic hydroxy compound represented by the structural formula:

R—[OH]$_m$ wherein R is an aromatic residue and m is at least 2, and said reaction product is at least difunctional and said difunctionality being epoxide.

2. The epoxy resin of claim 1 wherein R—[OH]$_m$ is selected from the group consisting of:

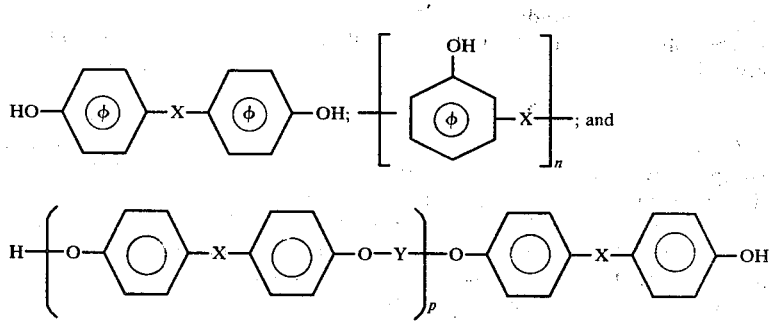

wherein X is alkylene having 1 to 3 carbon atoms, n and p are greater than 1, and Y is selected from the group consisting of:

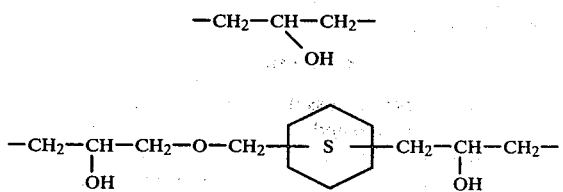

3. The epoxy resin of claim 1 having a weight per epoxide of about 450 to 6,000.

* * * * *